United States Patent
Gschneidner

(10) Patent No.: US 7,495,030 B2
(45) Date of Patent: *Feb. 24, 2009

(54) (5-(2-HYDROXY-4-CHLOROBENZOYL) AMINOVALERIC ACID AND SALTS THEREOF AND COMPOSITIONS CONTAINING THE SAME FOR DELIVERING ACTIVE AGENTS

(75) Inventor: David Gschneidner, Stamford, CT (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/363,726

(22) PCT Filed: Sep. 5, 2001

(86) PCT No.: PCT/US01/41985

§ 371 (c)(1),
(2), (4) Date: Mar. 6, 2003

(87) PCT Pub. No.: WO02/19969

PCT Pub. Date: Mar. 14, 2002

(65) Prior Publication Data

US 2004/0023847 A1 Feb. 5, 2004

Related U.S. Application Data

(60) Provisional application No. 60/237,234, filed on Oct. 2, 2000, provisional application No. 60/230,332, filed on Sep. 6, 2000.

(51) Int. Cl.
*A61K 31/19* (2006.01)
*A61K 31/195* (2006.01)
*A61K 38/00* (2006.01)
*A61K 31/715* (2006.01)
*C07C 229/00* (2006.01)

(52) U.S. Cl. .............................. 514/557; 514/2; 514/54; 514/563; 562/450; 562/455

(58) Field of Classification Search ................. 562/449, 562/450, 455; 514/2, 54, 557, 563
See application file for complete search history.

(56) References Cited

U.S. PATENT DOCUMENTS 5,583,020 A 12/1996 Sullivan
2004/0048777 A1* 3/2004 Weidner et al. ................. 514/2

FOREIGN PATENT DOCUMENTS

WO    WO 96/30036    10/1996
WO    WO00/07979    * 2/2000

OTHER PUBLICATIONS

Leon-Bay et al , Synthesis and Evaluation of compounds that facilitate the gastrointestinal absorption of Heparin, 1998, 41, p. 1163-1171.*
Grant et al , Chemical Dictionary, 1990, p. 305-306, and 159.*

* cited by examiner

*Primary Examiner*—Taylor Victor Oh
(74) *Attorney, Agent, or Firm*—Darby & Darby P.C.

(57) ABSTRACT

(5-(2-hydroxy-4-chlorobenzoyl) aminovaleric acid, salts thereof, and compositions containing the same for the delivery of active agents are provided. Methods of administration, treatment of disease and preparation are provided as well.

20 Claims, No Drawings

(5-(2-HYDROXY-4-CHLOROBENZOYL) AMINOVALERIC ACID AND SALTS THEREOF AND COMPOSITIONS CONTAINING THE SAME FOR DELIVERING ACTIVE AGENTS

This application is a national phase of PCT Application No. PGT/US01/41985, filed Sep. 5, 2001, which was published in English as International Publication No. WO 02/19969 and claims the benefit of U.S. Provisional Application Nos. 60/230,332 and 60/237,234, filed Sep. 6, 2000 and Oct. 2, 2000, respectively, both of which are herein incorporated by reference.

FIELD OF THE INVENTION

The present invention relates to (5-(2-hydroxy-4-chlorobenzoyl) aminovaleric acid and salts and polymeric derivatives thereof compounds for delivering active agents, such as biologically or chemically active agents, to a target. These compounds are well suited for forming non-covalent mixtures with active agents for oral, intracolonic, pulmonary, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e., active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

Proteinoid microspheres have been used to deliver pharmaceuticals. See, for example, U.S. Pat. Nos. 5,401,516; 5,443,841, and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Patent Publication No. WO 00/40203.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formula:

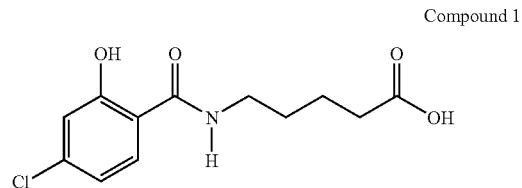

Compound 1 and salts thereof.

The invention also provides a composition comprising at least one of the delivery agent compound of the above formula, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at one of the delivery agent compounds of the formula above and the active agent to the animal. Preferred routes of administration include the oral, intracolonic and pulmonary routes.

Yet another embodiment is a method of treating a disease or for achieving a desired physiological effect in an animal in need thereof by administering an effective amount of the composition of the present invention.

Yet another embodiment is a method of preparing a composition of the present invention by mixing at least one delivery agent compound of the formula above, and at least one active agent.

DETAILED DESCRIPTION OF THE INVENTION

Delivery Agent Compounds

The terms "alkyl" and "alkenyl" as used herein include linear and branched alkyl and alkenyl substituents, respectively.

The delivery agent compounds may be in the form of the carboxylic acid or salts thereof. Suitable salts include, but are not limited to, organic and inorganic salts, for example alkalimetal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

Salts of the delivery agent compounds of the present invention may be prepared by methods known in the art. For example, sodium salts may be prepared by dissolving the delivery agent compound in ethanol and adding aqueous sodium hydroxide.

In addition, poly amino acids and peptides comprising one or more of these delivery agent compounds may be used.

An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

The compounds described herein may be derived from amino acids and can be readily prepared from amino acids by methods within the skill of those in the art based upon the present disclosure and the methods described in International Patent Publication Nos. WO96/30036 and WO97/36480 and U.S. Pat. Nos. 5,643,957 and 5,650,386. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, N.Y. (1981), the disclosure of which is hereby incorporated herein by reference.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, methanol, tetrahydrofuran and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

The delivery agent compound may contain a polymer conjugated to it by a linkage group selected from the group consisting of —NHC(O)NH—, —C(O)NH—, —NHC(O), —OOC—, —COO—, —NHC(O)O—, —OC(O)NH—, —CH$_2$NH —NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O)NH—, —NH—, —O—, and carbon-carbon bond. According to one preferred embodiment, with the proviso that the polymeric delivery agent is not a polypeptide or polyamino acid. The polymer may be any polymer including, but not limited to, alternating copolymers, block copolymers and random copolymers, which are safe for use in mammals. Preferred polymers include, but are not limited to, polyethylene; polyacrylates; polymethacrylates; poly(oxyethylene); poly(propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof. Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α, β and γ; interleukin-1, interleukin-2, insulin, including porcine, bovine, human, and human recombinant, optionally having counter ions including zinc, sodium, calcium and ammonium; insulin-like growth factor, including IGF-1, heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; antimicrobials, including antibiotics, anti-bacterials and antifungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

Delivery Systems

The composition of the present invention comprises one or more delivery agent compounds of the present invention (including their salts and polymeric derivatives), and one or more active agents. In one embodiment, one or more of the delivery agent compounds, or salts of these compounds, or poly amino acids or peptides of which these compounds or salts form one or more of the units thereof, may be used as a delivery may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the delivery agent compound with the solid form of the active agent. Alternately, a solid may be obtained from a solution of the delivery agent compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier. Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to, birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the delivery agent compounds and compositions of the present invention are useful in orally administering active agents, especially those that are not ordinarily orally deliverable, or those for which improved delivery is desired.

The compositions comprising the delivery agent compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54$^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
|---|---|
| Growth hormones | Growth disorders |
| Interferons, including α, β and γ. | Viral infection, including chronic cancer and multiple sclerosis |
| Interleukin-1; interleukin-2. | Viral infection; cancer |
| Insulin; Insulin-like growth factor IGF-1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone (PTH), including its fragments. | Osteoporosis; Diseases of the bone |
| Antimicrobials | Infection including gram-positive bacterial infection |
| Vitamins | Vitamin deficiencies |
| Bisphosphonates | Osteoporosis; Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-$d_6$) as the solvent unless otherwise indicated.

EXAMPLE 1

Compound Preparation

Preparation of Compound 1 (5-(2-Hydroxy-4-Chlorobenzoyl)Aminovaleric Acid)

A 1-liter, 3-neck flask equipped with a Dean-Stark trap and condenser was charged with 170.47 g (0.988 mol) of 4-chlorosalicylic acid, 510 ml (413.1 g, 5.57 mol) of n-butanol and 4.0 ml (7.36 g, 0.075 mol) of sulfuric acid. The suspension was heated to reflux. Over the course of 20 hours, 28 ml of water was removed via n-butanol azeotrope. The cooled reaction mixture was treated with 15 g of sodium bicarbonate, stirred for 30 minutes, washed with water (2×50 ml), dried over sodium sulfate and concentrated. A total of 232 g of butyl ester (and n-butanol) was isolated.

The ester and 800 ml of methanol were charged to a 2-liter, 3-neck flask equipped with an inlet attached to an ammonia cylinder and a reflux condenser. Gaseous ammonia was added periodically over 20-40 minutes every 4 hours or so. Addition caused the temperature to rise as high as 45° C. The progress of the reaction was monitored by HPLC. After 5 days and a total of 29 g (1.70 mol) of ammonia added, the reaction was complete. The reflux condenser was replaced by a distillation apparatus, and distillation of methanol and residual ammonia was begun. A total of 300 ml of distillate was collected. Upon cooling to 25° C. a solid formed. A total of 400 ml of water was added. The pH of the mixture was adjusted to 3.2 (from 9) with 4% aqueous hydrochloric acid. The solid was isolated by filtration, rinsing with 500 ml of 1:1 methanol/water, 200 ml of 4% aqueous sodium bicarbonate solution and 400 ml of 4:1 hexanes/ethyl acetate. A total of 142.64 g of 4-chlorosalicylamide was isolated.

A 1-liter flask equipped with an addition funnel was charged with 142.64 g (0.831 mol) of 4-chlorosalicylamide, 75 ml (73.35 g, 0.927 mol) of pyridine and 225 ml of acetonitrile. The slurry was cooled in an ice bath, and 86.0 ml (97.61 g, of 0.899 mol) of ethyl chloroformate was added dropwise over 50 minutes. The reaction mixture was stirred for 30 minutes and warmed to 25° C. The addition funnel was replaced by a distillation head. The mixture was refluxed for 20 hours, distilling 200 ml of solvent off in the last 4 hours. The cooled slurry was diluted with 300 ml of 2% aqueous sodium bicarbonate solution. The resulting solid was filtered off to give 149.91 g of 7-chlorocarsalm, after drying.

A 100 ml flask equipped with a reflux condenser was charged with 4.47 g (22.6 mmol) of 7-chlorocarsalam, 3.55 ml (4.69 g, 22.4 mmol) of ethyl 5-bromovalerate, 35 ml of dimethylacetamide and 2.47 g (23.3 mmol) of sodium carbonate. The suspension was heated to 70° C. After 3 hours, the reaction was complete. The cooled reaction mixture was filtered, rinsing with ethanol. The filtrate was diluted with 200 ml of water, causing a solid to develop. The solid was isolated by filtration. The wet cake was taken up in 20 ml of ethanol and 40 ml of 2N aqueous sodium hydroxide solution. After refluxing for 3 hours, the mixture was cooled to 25 C and acidified with 4% aqueous hydrochloric acid. The resulting solid was isolated by filtration and recrystallized to give 4.83 g of 5-(2-hydroxy-4-chlorobenzoyl)aminovaleric acid, mp 140-1° C. Combustion analysis: % C: 53.05 (calc'd), 52.91 (found); % H: 5.19 (calc'd), 5.01 (found); % N: 5.16 (calc'd), 5.02 (found). 1H NMR Analysis: (d6-DMSO): δ 13.0, s, 1H (COOH); δ 12.1, s, 1H (OH); δ 8.9, t, 1H, (NH); δ 7.9, d, 1H (aryl H ortho to amide); δ 7.0, m, 2H (other two aryl H); δ 3.3, q, 2H, ($CH_2$ α to N); δ 2.3, t, 2H ($CH_2$ α to COOH); δ 1.6, m, 4H (other two CH2's).

EXAMPLE 2

Cromolyn—Oral Delivery

Dosing solutions containing a delivery agent compound and cromolyn, disodium salt (cromolyn)(from Sigma Chemical of St. Louis, Mo.) were prepared in deionized water. The free acid of the delivery agent compound was converted to the sodium salt with one equivalent of sodium hydroxide. This mixture was vortexed and placed in a sonicator (about 37° C.). The pH was adjusted to about 7-7.5 with aqueous NaOH. Additional NaOH was added, if necessary, to achieve uniform solubility, and the pH re-adjusted. The mixture was vortexed to produce a uniform solution, also using sonication and heat if necessary. The delivery agent compound solution was mixed with cromolyn from a stock solution (175 mg cromolyn/ml in deionized water, pH adjusted, if necessary, with NaOH or HCl to about 7.0, stock solution stored frozen wrapped in foil, then thawed and heated to about 30° C. before using). The mixture was vortexed to produce a uniform solution, also using sonication and heat if necessary. The pH was adjusted to about 7-7.5 with aqueous NaOH. The solution was then diluted with water to the desired volume (usually 2.0 ml) and concentration and stored wrapped in foil before use. The final delivery agent compound and cromolyn doses, and the dose volumes are listed below in Table 1.

The typical dosing and sampling protocols were as follows. Male Sprague-Dawley rats weighing between 200-250 g were fasted for 24 hours and were anesthetized with ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected via the tail artery, typically at 0.25, 0.5, 1.0 and 1.5 hours after dosing. Serum cromolyn concentrations were measured by HPLC. Samples were prepared as follows: 100 µl serum was combined with 100 µl 3N HCl and 300 µl ethyl acetate in an eppendorf tube. The tube was vortexed for 10 minutes and then centrifuged for minutes at 10,000 rpm. 200 µl ethyl acetate layer was transferred to an eppendorf tube containing 67 βl 0.1 M phosphate buffer. The tube was vortexed for 10 minutes and then centrifuged for minutes at 10,000 rpm. The phosphate buffer layer was then transferred to an HPLC vial and injected into the HPLC (column=Keystone Exsil Amino 150×2 mm i.d., 5 µm, 100 Å; mobile phase=35% buffer(68 mM $KH_2PO_4$ adjusted to pH 3.0 with 85% $H_3PO_4$)/65% acetonitrile; injection volume=10 µl; flow rate=0.30 ml/minute; cromolyn retention time=5.5 minutes; absorbance detected at 240 nm). Previous studies indicated baseline values of about zero.

Results from the animals in each group were averaged for each time point and the highest of these averages (i.e., mean peak serum cromolyn concentration) is reported below in Table 1.

TABLE 1

| | Cromolyn - Oral Delivery | | | |
|---|---|---|---|---|
| Compound | Compound Dose (mg/kg) | Cromolyn Dose (mg/kg) | Volume dose (ml/kg) | Mean Peak serum [cromolyn] µg/ml ± SD |
| 1 | 200 | 25 | 1 | 0.36 ± 0.42 |
| 1 | 200 | 25 | 1 | 0.08 ± 0 |

EXAMPLE 3

Interferon—Oral Delivery

Dosing solutions of the delivery agent compound and human interferon (IFN) were prepared in deionized water. The free acid of the delivery agent compound was converted to the sodium salt with one equivalent of sodium hydroxide. Typically, a solution of the delivery agent compound was prepared in water and stirred, adding one equivalent of sodium hydroxide (1.0 N) when making the sodium salt. This mixture was vortexed and placed in a sonicator (about 37° C.). The pH was adjusted to about 7.0 to 8.5 with aqueous NaOH. The mixture was vortexed to produce a uniform suspension or solution, also using sonication and heat if necessary. Additional NaOH was added, if necessary, to achieve uniform solubility, and the pH re-adjusted. The delivery agent compound solution was mixed with an IFN stock solution (about 22.0 to 27.5 mg/ml in phosphate buffered saline) and diluting to the desired volume (usually 3.0 ml). The final delivery agent compound and IFN doses, and the dose volumes are listed below in Table 2.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=0, 15, 30, 45, 60 and 90 minutes. Serum IFN concentrations were quantified using Cytoscreen Immunoassay Kit for human IFN-alpha (catalog # KHC4012 from Biosource International, Camarillo, Calif.). Previous studies indicated baseline values of about zero. Results from the animals in each group were averaged for each time point. The maximum of these averages (i.e., the mean peak serum IFN concentration) is reported below in Table 2.

TABLE 2

| | Interferon - Oral Delivery | | | |
|---|---|---|---|---|
| Compound | Compound Dose (mg/kg) | IFN Dose (mg/kg) | Volume dose (ml/kg) | Mean Peak Serum [IFN] (ng/ml) ± SD |
| 1 | 200 | 1.0 | 1.0 | 9.90 ± 4.59 |

Example 4

Insulin—Oral Delivery

Oral dosing (PO) compositions of delivery agent compound and human zinc insulin (minimum 26 IU/mg available from Calbiochem—Novabiochem Corp, La Jolla, Calif.) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted.

Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The final delivery agent compound dose, insulin dose and dose volume amounts are listed below in Table 3.

The typical dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=15, 30, 60, 120 and 180 minutes. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations (pU/ml) were measured for each time point for each of the five animals in each dosing group. The five values for each time point were averaged and the results plotted as serum insulin concentration versus time. (Previous experiments revealed no measurable levels of human insulin following oral dosing with human insulin alone.) Serum glucose levels were also measured. The maximum (peak) are reported below in Table 3.

TABLE 3

| | Insulin - Oral Delivery | | | | |
|---|---|---|---|---|---|
| Delivery Agent Compound # | Delivery Agent Compound Dose (mg/kg) | Insulin Dose (mg/kg) | Volume dose (ml/kg) | Mean Peak Serum Human Insulin (μU/ml ± SD) | Mean Peak Serum Glucose Levels (μU/ml) |
| 1 | 200 | 0.5 | 1.0 | 6.40 ± 3.18 | 36.25 ± 2.5 |

EXAMPLE 5

Daptomycin—Oral/Intracolonic Delivery

Dosing solutions containing a delivery agent compound and daptomycin (Cubist Pharmaceuticals, Cambridge, Mass.) were prepared in 0.9% normal saline. A solution of the compound was made either with the sodium salt of the compound or by converting the free acid to its sodium salt. The free acid of the delivery agent compound was converted to the sodium salt with one equivalent of sodium hydroxide. This mixture was vortexed and placed in a sonicator (about 37° C.). The pH was adjusted to about 7.0-7.5 with aqueous HCl or NaOH. Additional NaOH was added, if necessary, to achieve uniform solubility, and the pH readjusted. The mixture was vortexed to produce a uniform solution, also using sonication if necessary. The delivery agent compound solution was mixed with daptomycin from a stock solution (200 mg daptomycin/mL in 0.9% normal saline and the pH adjusted, if necessary, to between 6.0-7.0 with NaOH or HCl). The stock solution was stored frozen (−20° C.) wrapped in foil, then thawed and warmed gradually to about 25° C. before using. The delivery agent-daptomycin mixture was vortexed at low speed to produce a uniform solution. The pH was adjusted to about 7.0-7.5 with aqueous NaOH. The solution was then diluted with 0.9% normal saline to the desired volume (usually 2.0 ml) and concentration and stored wrapped in foil before use. The final delivery agent compound and daptomycin doses, and the dose volumes are listed below in Table 4.

The typical dosing and sampling protocols were as follows. Male Sprague-Dawley rats weighing between 200-250 g were fasted for 24 hours and were anesthetized with ketamine (44 mg/kg) and thorazine (1.5 mg/kg) 15 minutes prior to dosing and again as needed to maintain anesthesia. A dosing group of five animals was administered one of the dosing solutions. For oral gavage (PO) dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger. For intracolonic (IC) dosing, a 7.5 cm, 8 fr Rusch catheter was adapted to a 1 ml syringe with a pipette tip. The dosing catheter was inserted into the colon through the anus until the tube was no longer visible. The dosing solution was expressed slowly into the colon by pressing the syringe plunger.

Heparinized rat blood samples were collected via the ventral tail artery, typically at 0.25, 0.5, 0.75, 1.0, 2.0, and 4.0 hours after dosing, and stored on ice. Blood samples were then spun (centrifuged) at 11,500 rpm for 4 minutes at 4° C. to obtain the plasma (supernatant), which was stored at −70° C. The plasma daptomycin concentrations were measured by isocratic reversed phase HPLC, keeping samples at 4° C. during analysis. Blank plasma studies show baseline values of zero.

Results from the animals in each group were averaged for each time point and the highest of these averages (i.e., mean peak daptomycin concentration, $C_{max}$) is reported below in Table 4.

TABLE 4

Daptomycin - Oral Delivery

| Delivery Agent Compound | Route of Administration | Delivery Agent Compound Dose (mg/kg) | Daptomycin Dose (mg/kg) | Volume dose (mL/kg) | Mean Plasma Cmax [daptomycin] ± SD, µg/mL |
|---|---|---|---|---|---|
| 1 | PO | 200 | 50 | 1 | 9.82 ± 6.80 |
| 1 | IC | 200 | 25 | 1 | 26.24 ± 2.78 |
| 1 | PO | 200 | 50 | 1 | 12.74 ± 8.37 |
| 1 | PO | 200 | 50 | 1 | 19.12 ± 3.05 |
| 1 | PO | 200 | 50 | 2 | 13.38 ± 3.53 |

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound selected from the group consisting of

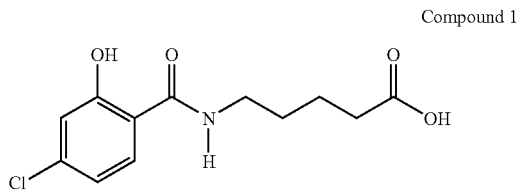

Compound 1 and salts thereof.

2. A composition comprising:
(A) a biologically active agent; and
(B) a compound selected from the group consisting of

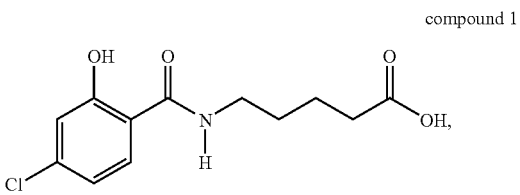

compound 1 salts thereof, and mixtures thereof.

3. The composition of claim 2, wherein the biologically active agent is at least one protein, polypeptide, peptide, hormone, polysaccharide, mucopolysaccharide, carbohydrate, or lipid.

4. The composition of claim 2, wherein the biologically active agent is selected from the group consisting of:
growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erytliropojetin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, fligrastim, prostaglandins, cyclosporin, vasopressin, cromolyn sodium, sodium chromoglycate, disodium chromoglycate, vancomycin, desferrioxamine (DFO), parathyroid hormone (PTH), antimicrobials, antibiotics, antibacterial agents, anti-fungal agents, daptomycin, and vitamins; and any combination thereof.

5. The composition of claim 2, wherein the biologically active agent is selected from the group consisting of interferon, cromolyn sodium, sodium chromoglycate, disodium chromoglycate, and daptomycin, or a combination thereof.

6. The composition of claim 2, wherein the biologically active agent is interferon.

7. The composition of claim 2, wherein the biologically active agent is cromolyn sodium.

8. The composition of claim 2, wherein the biologically active agent is daptomycin.

9. A dosage unit form comprising:
(A) the composition of claim 2; and
(B) (a) an excipient
(b) a diluent,
(c) a disintegrant,
(d) a lubricant,
(e) a plasticizer,
(f) a colorant,
(g) a dosing vehicle, or
(h) any combination thereof.

10. The dosage unit form of claim 9, wherein the biologically active agent is a protein, polypeptide, peptide, hormone, polysaccharide, mucopolysaccharide, carbohydrate, or lipid.

11. The dosage unit form of claim 9, wherein the biologically active agent is selected from the group consisting of:
growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, fligrastim, prostaglandins, cyclosporin, vasopressin, cromolyn sodium, sodium chromoglycate, disodium chromoglycate, vancomycin, desferrioxamine (DFO), parathyroid hormone (PTH), antimicrobials, antibiotics, antibacterial agents, anti-fungal agents, daptomycin, and vitamins; and any combination thereof.

12. The dosage unit form of claim 9, wherein the biologically active agent is selected from the group consisting of interferon, cromolyn sodium, sodium chromoglycate, disodium chromoglycate and daptomycin, or a combination thereof.

13. The dosage unit form of claim 9, wherein the biologically active agent is interferon.

14. The dosage unit form of claim 9, wherein the biologically active agent is cromolyn sodium.

15. The dosage unit form of claim 9, wherein the biologically active agent is daptomycin.

16. The dosage unit form of claim 9, wherein the dosage unit form is in the form of a tablet, a capsule, a particle, a powder, a sachet, or a liquid.

17. The dosage unit form of claim 9, wherein the dosing vehicle is liquid selected from the group consisting of water, 25% aqueous propylene glycol, phosphate buffer, 1,2-propane diol, ethanol, and any combination thereof.

18. A method for preparing a composition comprising mixing:
   (A) at least one biologically active agent;
   (B) the compound of claim 1; and
   (C) optionally, a dosing vehicle.

19. The method according to claim 18, wherein the biologically active agent is at least one protein, polypeptide, peptide, hormone, polysaccharide, mucopolysaccharide, carbohydrate, or lipid.

20. The method according to claim 19, wherein the biologically active agent is selected from the group consisting of: growth hormones, human growth hormones (hGH), recombinant human growth hormones (rhGH), bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine (DFO), parathyroid hormone (PTH), antimicrobials, antibiotics, antibacterial agents, anti-fungal agents, daptomycin, and vitamins; and any combination thereof.

* * * * *